(12) United States Patent
Mackay (10) Patent No.: US 10,186,406 B2
(45) Date of Patent: Jan. 22, 2019

(54) MULTI-CHANNEL PHOTOMULTIPLIER TUBE ASSEMBLY

(71) Applicant: KLA—Tencor Corporation, Milpitas, CA (US)

(72) Inventor: Derek Mackay, Menlo Park, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 0 days.

(21) Appl. No.: 15/268,326

(22) Filed: Sep. 16, 2016

(65) Prior Publication Data

US 2017/0287686 A1   Oct. 5, 2017

Related U.S. Application Data

(60) Provisional application No. 62/314,654, filed on Mar. 29, 2016.

(51) Int. Cl.
*H01J 40/14* (2006.01)
*H01J 43/20* (2006.01)
(Continued)

(52) U.S. Cl.
CPC .......... *H01J 43/20* (2013.01); *G01N 21/8806* (2013.01); *G01N 21/9501* (2013.01)

(58) Field of Classification Search
CPC .. G01N 21/8806; G01N 21/9501; H01J 43/20
(Continued)

(56) References Cited

U.S. PATENT DOCUMENTS 4,931,704 A * 6/1990 Alfano .................. G01R 13/34
313/532
5,111,051 A   5/1992 Watanabe
(Continued)

FOREIGN PATENT DOCUMENTS

WO   2015100421 A1   7/2015

OTHER PUBLICATIONS

Dmytro Gudkov et al., Enhancing the Linear Dynamic Range in Multi-Channel Single Photon Detector Beyond 7OD, IEEE Sensors Journal, vol. 15, No. 12, Dec. 2015, pp. 7081-7086.
(Continued)

*Primary Examiner* — Kevin Pyo
(74) *Attorney, Agent, or Firm* — Suiter Swantz pc llo (57) ABSTRACT

A multi-channel photomultiplier tube (PMT) detector assembly includes a photocathode. The detector assembly includes a first dynode channel including a first set of dynode pathways. The first set of dynode pathways include a plurality of dynode stages configured to receive a first portion of the photoelectrons and direct a first amplified photoelectron current onto a first anode. The detector assembly includes an additional dynode channel including an additional set of dynode pathways. The additional set of dynode pathways includes a plurality of dynode stages configured to receive an additional portion of the photoelectrons and direct an additional amplified photoelectron current onto an additional anode. The detector assembly includes a grid configured to direct the first portion of the photoelectrons to one or more of the first set of pathways and an additional portion of the photoelectrons to one or more of the additional set of pathways.

18 Claims, 8 Drawing Sheets

(51) Int. Cl.
*G01N 21/88* (2006.01)
*G01N 21/95* (2006.01)

(58) Field of Classification Search
USPC ..... 250/207, 214 VT; 313/103 CM, 105 CM
See application file for complete search history.

(56) References Cited

U.S. PATENT DOCUMENTS

| | | |
|---|---|---|
| 7,130,036 B1 | 10/2006 | Kuhlmann et al. |
| 8,139,840 B1 | 3/2012 | Chu et al. |
| 2002/0161534 A1 | 10/2002 | Adler et al. |
| 2003/0127582 A1 | 7/2003 | Jones |
| 2004/0069932 A1* | 4/2004 | Kato ............... H01J 43/045 |
| | | 250/214 VT |
| 2010/0096560 A1 | 4/2010 | Imanishi et al. |
| 2013/0169957 A1 | 7/2013 | Wolf et al. |
| 2013/0242291 A1 | 9/2013 | Eaton |
| 2013/0264464 A1 | 10/2013 | Heifets et al. |
| 2015/0136948 A1 | 5/2015 | Mackay et al. |

OTHER PUBLICATIONS

Ken Kaufmann, Hamamatsu Corporation, Photomultipliers: Low-Light, High-Speed Specialists, Printed online: http://www.photonics.com/EDU/Handbook.aspx?AID=25145, Print Date Apr. 4, 2016, pp. 1-5.

* cited by examiner

MULTI-CHANNEL PHOTOMULTIPLIER TUBE ASSEMBLY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled MULTI-CHANNEL ULTRA HIGH SPEED PHOTOMULTIPLIER TUBE, naming Derek Mackay as inventor, filed Mar. 29, 2016, Application Ser. No. 62/314,654.

TECHNICAL FIELD

The present invention generally relates to a photomultiplier tube detector assembly, and more particularly, to a multi-channel photomultiplier tube detector assembly.

BACKGROUND

As demand for semiconductor devices increase the need for improved device inspection capabilities will also continue to increase. One technology commonly utilized in optical inspection methodologies includes the implementation of a photomultiplier tube (PMT) detector. In a general sense, photomultiplier tube detectors are sensitive detectors of light in the UV, visible, and near-infrared ranges of the electromagnetic spectrum. Therefore, PMTs are widely utilized for semiconductor device inspection processes. One commonly implemented design includes a single channel PMT (e.g., circular-cage type, box- and grid type, and linear focused type). Such a single channel PMT suffers from diminished speed of a detection.

Therefore, it is desirable to create a photomultiplier tube detector assembly that cures the shortcomings of the prior approach.

SUMMARY

A photomultiplier tube detector assembly is disclosed, in accordance with one or more illustrative embodiments of the present disclosure. In one embodiment, the photomultiplier tube detector assembly includes a photocathode configured to absorb photons, the photocathode is further configured to emit photoelectrons. In another embodiment, the photomultiplier tube detector assembly includes a first dynode channel, the first dynode channel including a first set of dynode pathways, at least some of the first set of dynode pathways including a plurality of dynode stages configured to receive a first portion of the photoelectrons and direct a first amplified photoelectron current onto a first anode of a first set of anodes. In another embodiment, the photomultiplier tube detector assembly includes an additional dynode channel, the additional dynode channel including an additional set of dynode pathways, at least some of the additional set of dynode pathways including a plurality of dynode stages configured to receive an additional portion of the photoelectrons and direct an additional amplified photoelectron current onto an additional anode of an additional set of anodes. In another embodiment, the photomultiplier tube detector assembly includes a grid configured to direct the first portion of the photoelectrons emanating from the photocathode to one or more of the first set of pathways of the first dynode channel. In another embodiment, the grid is further configured to direct the additional portion of the photoelectrons emanating from the photocathode to one or more of the additional set of pathways of the additional dynode channel.

An inspection system is disclosed in accordance with one or more illustrative embodiments of the present disclosure. In one embodiment, the inspection system includes an illumination source configured to illuminate a portion of a sample surface. In another embodiment, the inspection system includes a set of illumination optics configured to direct and focus the illumination onto the sample surface. In another embodiment, the inspection system includes a photomultiplier tube detector assembly. In another embodiment, the photomultiplier tube detector assembly includes a photocathode configured to absorb photons, the photocathode further configured to emit photoelectrons. In another embodiment, the photomultiplier tube detector assembly includes a first dynode channel, the first dynode channel including a first set of dynode pathways, at least some of the first set of dynode pathways including a plurality of dynode stages configured to receive a first portion of the photoelectrons and direct a first amplified photoelectron current onto a first anode of a first set of anodes. In another embodiment, the photomultiplier tube detector assembly includes an additional dynode channel, the additional dynode channel including an additional set of dynode pathways, at least some of the additional set of dynode pathways including a plurality of dynode stages configured to receive an additional portion of the photoelectrons and direct an additional amplified photoelectron current onto an additional anode of an additional set of anodes. In another embodiment, the photomultiplier tube detector assembly includes a grid configured to direct the first portion of the photoelectrons emanating from the photocathode to one or more of the first set of pathways of the first dynode channel. In another embodiment, the grid is further configured to direct the additional portion of the photoelectrons emanating from the photocathode to one or more of the additional set of pathways of the additional dynode channel.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, and serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 3, a multi-channel photomultiplier tube (PMT) detector assembly 100 is described in accordance with the present disclosure. Embodiments of the present disclosure are directed to a multi-channel photomultiplier tube (PMT) detector assembly 100 having multiple channels arranged in a parallel pattern to enhance inspection bandwidth. Embodiments of the present disclosure are particularly useful in the context of semiconductor inspection. Embodiments of the present disclosure provide for the rapid measurement of adjacent samples or different areas of the same sample. The multi-channel structure of the PMT detector assembly 100 of the present disclosure increases inspection speed by multiple times compared to conventional single-channel PMT detectors.

Figure 1A:
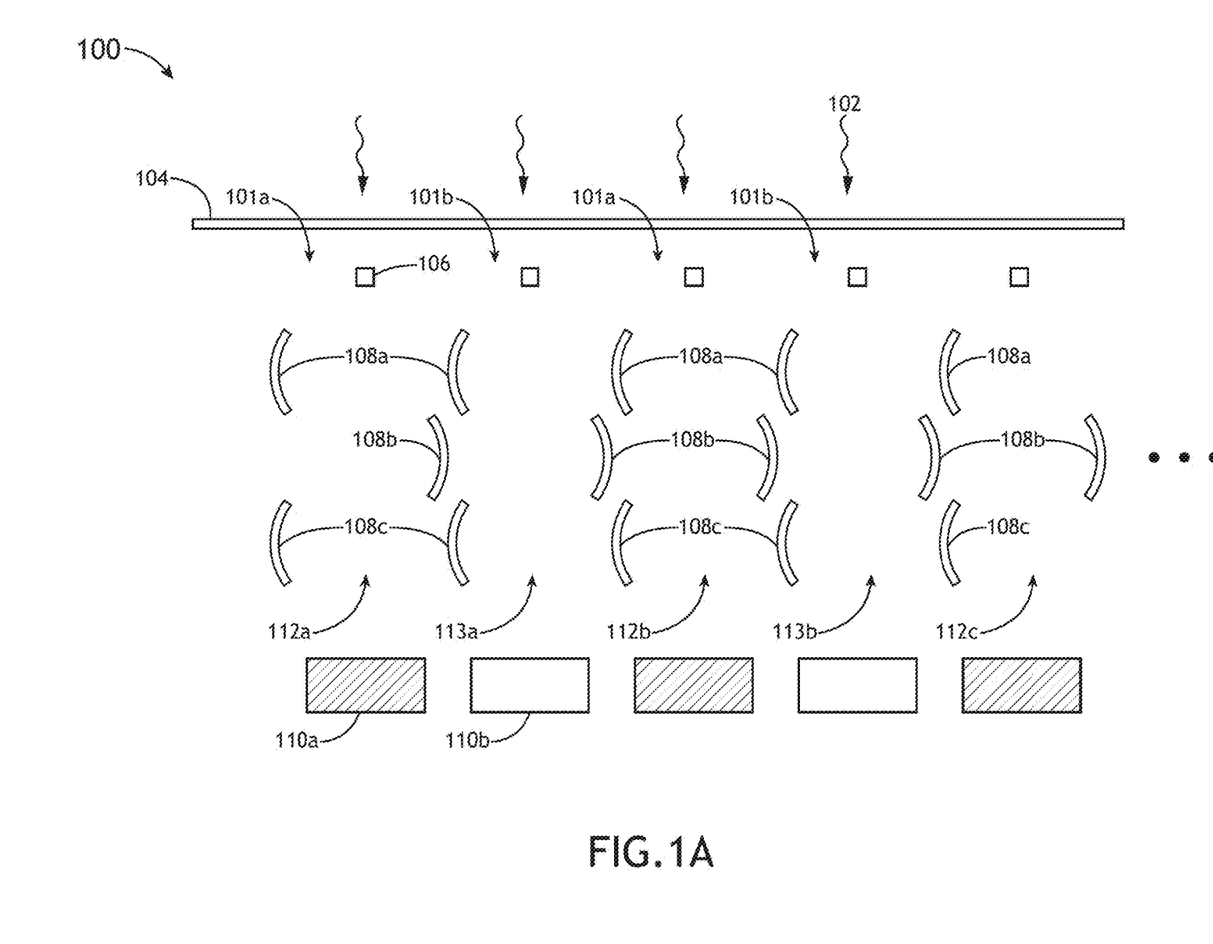
FIG. 1A illustrates a simplified schematic view of a multi-channel photomultiplier tube detector assembly, in accordance with one or more embodiments of the present disclosure.

FIG. 1A illustrates a simplified view of a multi-channel PMT detector assembly 100, in accordance with one or more embodiments of the present disclosure. In one embodiment, the multi-channel PMT detector assembly 100 includes a photocathode 104. In one embodiment, the photocathode 104 absorbs one or more portions of photons 102 and then, in response to the absorption of the one or more portions of photons 102, emits one or more portions of photoelectrons.

In another embodiment, the multi-channel PMT detector assembly 100 includes a first dynode channel 101a and a second dynode channel 101b arranged in parallel. For example, the first dynode channel 101a and the second dynode channel 101b may each be defined by multiple pathways. For instance, the first dynode channel 101a may include a set of dynode pathways 112a-112c. In another instance, the second dynode channel 101b may include a set of dynode pathways 113a-113b. Further, as shown in FIG. 1A, the first dynode pathways 112a-112c of the first dynode channel 101a and the second dynode pathways 113a-113b of the second dynode channel 101b may be arranged in an interleaving parallel pattern.

It is contemplated that, while the first dynode channel 101a and the second dynode channel 101b are depicted in a two-channel parallel arrangement, as shown in FIG. 1A, such an arrangement is merely provided for illustrative purposes. It is noted that the detector assembly 100 may include any number of dynode channels, such as three- or more-channels arranged in parallel (e.g., an interleaving parallel pattern).

It is further contemplated that, while the first dynode pathways 112a-112c of the first dynode channel 101a and the second dynode pathways 113a-113b of the second dynode channel 101b are shown in FIG. 1A as a stack of five dynode pathways (i.e., 112a, 112b, 112c, 113a, and 113b), such a configuration is merely provided for illustrative purposes. It is noted that each dynode channel may include any number of dynode pathways, whereby pathways from each channel are arranged in an interleaving parallel pattern.

In one embodiment, one or more portions of the first photoelectrons emitted by the photocathode 104 enter the first pathways 112a-112c of the first dynode channel 101a, while one or more portions of the second photoelectrons emitted by the photocathode 104 enter the second dynode pathways 113a-113b of the second dynode channel 101b sequentially. In another embodiment, one or more portions of the first photoelectrons enter the first pathways 112a-112c of the first dynode channel 101a, while one or more portions of the second photoelectrons enter the second dynode pathways 113a-113b of the second dynode channel 101b simultaneously.

In another embodiment, the multi-channel PMT detector assembly 100 includes a grid 106 for controlling and/or directing one or more portions of the photoelectrons emitted by the photocathode 104. For example, the grid 106 may be located proximately to the portion of the photocathode 104. For instance, the location of the grid 106 relative to the photocathode 104 and the first and second channels 101a, 101b may be selected so that the one or more portions of the photoelectrons emitted from the photocathode 104 may be efficiently directed into the first channel 101a and/or second channel 101b. It is noted that scope of the present disclosure is not limited to controlling the entrance of the one or more portions of the photoelectrons into the first pathways 112a-112c of the first channel 101a and the second pathways 113a-113b of the second channel 101b with the grid 106, which is provided merely for illustrative purposes. Rather, it is recognized herein that the multi-channel PMT detector assembly 100 may control the entrance of the one or more portions of the photoelectrons into the first pathways 112a-112c of the first channel 101a and the second pathways 113a-113b of the second channel 101b using any electron control means known in the art, such as, but not limited to, one or more focusing electrodes or one or more focusing meshes.

In another embodiment, each of the pathways 112a, 112b, 112c of the first channel 101a of the multi-channel PMT detector assembly 100 include a plurality of dynode stages 108a-108c. In another embodiment, each of the pathways 113a, 113b of the second channel 101b of the multi-channel PMT detector assembly 100 also include a plurality of dynode stages 108a-108c. For example, the plurality of the dynode stages 108a-108c of the first channel 101a and the second channel 101b may be configured to receive one or more portions of the photoelectrons emitted by the photocathode 104. For instance, the plurality of the dynode stages 108a-108c of the first channel 101a and the second channel 101b may be further configured to amplify the one or more portions of the photoelectrons. In another instance, the plurality of the dynode stages 108a-108c of the first channel 101a and the second channel 101b are configured to direct the amplified photoelectron current onto a set of anodes 110a, 110b.

In another embodiment, the multi-channel PMT detector assembly 100 includes a first set of anodes 110a and a second set of anodes 110b arranged to collect one or more amplified photoelectron currents from the first dynode pathways 112a-112c of the first dynode channel 101a and the second dynode pathways 113a-113b of the second dynode channel 101b, respectively. For example, the first set of anodes 110a associated with the first dynode pathways 112a-112c of the first dynode channel 101a and the second set of anodes 110b associated with the second dynode pathways 113a-113b of the second dynode channel 101b may be arranged in parallel. In this regard, the parallel arrangement of the first and second set of anodes 110a, 110b may correspond with the parallel arrangement of the first dynode channels 101a and the second dynode channel 101b, as shown in FIG. 1A.

By way of another example, the anodes of the first set of anodes 110a associated with the first dynode pathways 112a-112c of the first dynode channel 101a may be aligned with the first dynode pathways 112a-112c of the first dynode channel 101a to collect the one or more amplified photoelectron currents in the first dynode pathways 112a-112c of the first dynode channel 101a. In this regard, the anodes of the first set of anodes 110a associated with the first dynode pathways 112a-112c of the first dynode channel 101a may be positioned directly below the first dynode pathways 112a-112c of the first dynode channel 101a. By way of yet another example, the anodes of the second set of anodes 110b associated with the second dynode pathways 113a-113b of the second dynode channel 101b may be aligned with the second dynode pathways 113a-113b of the second dynode channel 101b to collect the one or more amplified photoelectron currents in the second dynode pathways 113a-113b of the second dynode channel 101b. In this regard, the anodes of the second set of anodes 110b associated with the second dynode pathways 113a-113b of the second dynode channel 101b may be positioned directly below the second dynode pathways 113a-113b of the second dynode channel 101b. Furthermore, the location of the first set of anodes 110a and the second set of the anodes 110b relative to the dynode pathways 112a-112c, 113a-113b may be selected so that the amplified photoelectron currents emanating from the plurality of the dynode stages 108a-108c may be efficiently directed into the first set of the anodes 110a and the second set of the anodes 110b.

It is contemplated that, while the first set of the anodes 110a and the second set of the anodes 110b described above are shown as physically separated anodes from the simplified view shown in FIG. 1A, such a configuration is merely provided for illustrative purposes. For example, all of the first set of the anodes 110a may be shorted together. By way of another example, all of the second set of the anodes 110b may be shorted together. Any shorting techniques known in the art may be employed in order to short individual anodes together.

Further, the first set of the anodes 110a associated with the first dynode pathways 112a-112c of the first dynode channel 101a and the second set of the anodes 110b associated with the second dynode pathways 113a-113b of the second dynode channel 101b may include one or more phosphor coated anodes suitable for converting the one or more photoelectron currents into one or more light signals. For example, the one or more phosphor coated first and second set of the anodes 110a, 110b may be energized by the one or more amplified photoelectron currents. In another embodiment, the multi-channel PMT detector assembly 100 includes one or more detectors (not shown) configured to detect the one or more light signals emanating from the first set of the anodes 110a associated with the first dynode pathways 112a-112c of the first dynode channel 101a and the second set of the anodes 110b associated with the second dynode pathways 113a-113b of the second dynode channel 101b. For example, the one or more detectors may include any detector known in the art, such as, but not limited to, a charge-coupled device (CCD) detector, or a complementary metal oxide-semiconductor (CMOS) detector.

FIGS. 1B-1F illustrate the multi-channel PMT detector assembly 100 operating in a first configuration and second configuration, whereby one or more portions of first and second photoelectrons 114, 122 are directed along the first channel 101a and the second channel 101b, respectively, in accordance with one or more embodiments of the present disclosure.

Figure 1B:
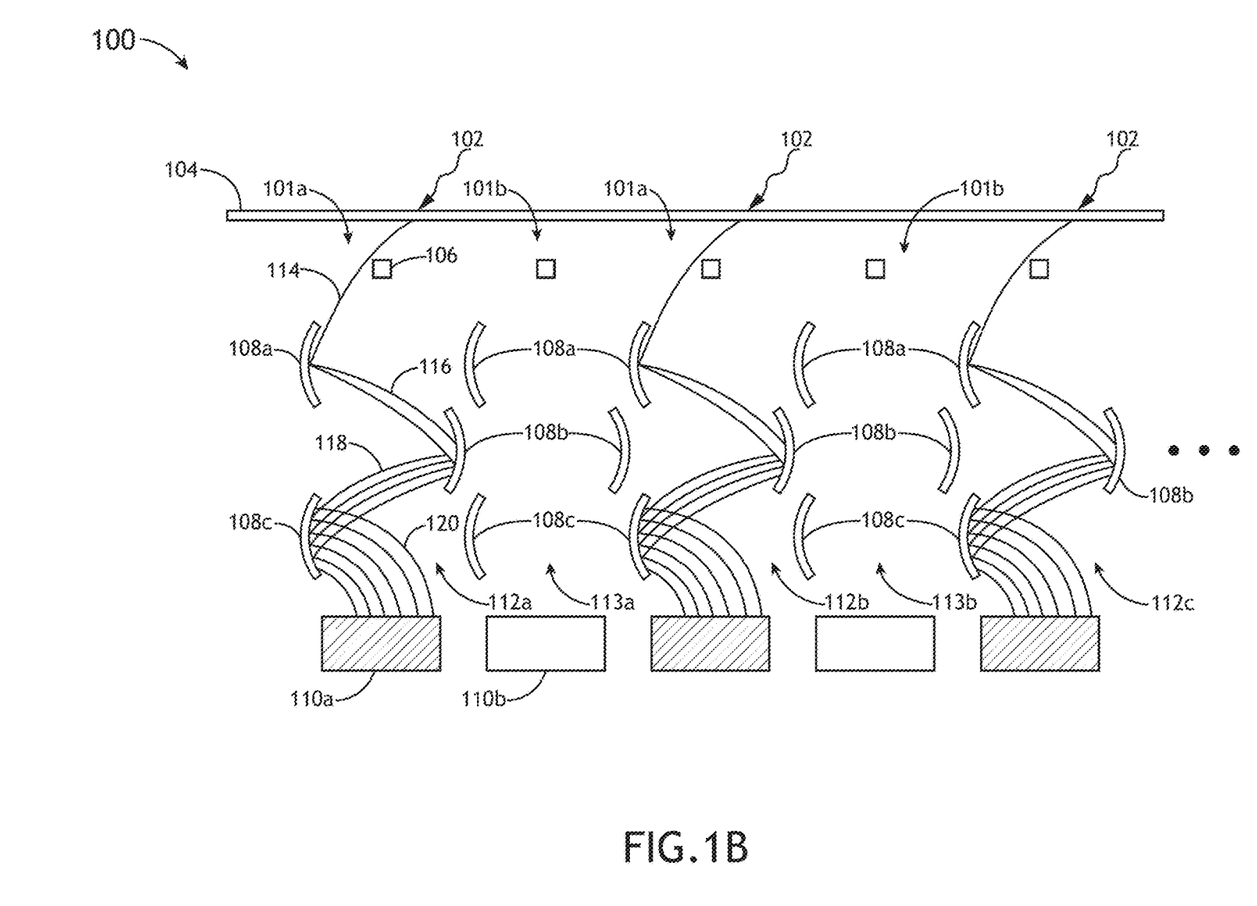
FIG. 1B illustrates a simplified schematic view of a multi-channel photomultiplier tube detector assembly depicting amplification of one or more portions of first photoelectrons in a first dynode channel, in accordance with one or more embodiments of the present disclosure.

FIG. 1B illustrates a simplified schematic view of the multi-channel PMT detector assembly 100 depicting amplification of one or more portions of first photoelectrons 114 emitted by the photocathode 104 in the first dynode pathways 112a-112c of the first channel 101a, in accordance with one or more embodiments of the present disclosure. It is noted herein that the various embodiments, components and architecture described previously herein should be interpreted to extend to the multi-channel PMT detector assembly 100 of FIG. 1B.

In one embodiment, the multi-channel PMT detector assembly 100 includes the plurality of the dynode stages 108a-108c configured to amplify the one or more potions of the first photoelectrons 114 emitted by the photocathode 104. For example, the first set of the plurality of the dynode stages 108a associated with the first dynode pathways 112a-112c of the first dynode channel 101a may be configured to receive the one or more portions of the first photoelectrons 114 converted from a photon 102 by the photocathode 104. For instance, the first set of the plurality of the dynode stages 108a associated with the first dynode pathways 112a-112c of the first dynode channel 101a may be further configured to direct and/or amplify the one or more portions of the first photoelectrons 114 via secondary emission such that first amplified photoelectron currents 116 emanating from the first set of the plurality of the dynode stages 108a associated with the first dynode pathways 112a-112c of the first dynode channel 101a is larger than the one or more portions of the first photoelectrons 114 emitted by the photocathode 104. In turn, the second set of the plurality of the dynode stages 108b associated with the first dynode pathways 112a-112c of the first dynode channel 101a may amplify the first amplified photoelectron currents 116 such that a second amplified photoelectron currents 118 is larger than the first amplified photoelectron currents 116. This process can be carried out multiple times, thereby building up the amplified photoelectron currents to desired levels. Upon undergoing amplification at the each of the multiple dynode stages associated with the first dynode pathways 112a-112c of the first dynode channel 101a, the second amplified photoelectron currents 118 may be directed by the set of third dynode stages 108c associated with the first dynode pathways 112a-112c of the first dynode channel 101a such that amplified photoelectron outputs 120 impinge on the first set of anode 110a.

It is noted that the one or more portions of the first photoelectrons 114 emitted by the photocathode 104 may reach the first set of the plurality of the dynode stages 108a associated with all of the first dynode pathways 112a-112c of the first dynode channel 101a at the same time, while the second dynode pathways 113a-113b of the second dynode channel 101b does not receive the one or more portions of the first photoelectrons 114 emitted by the photocathode 104. In this regard, the one or more portions of the first photoelectrons 114 emitted by the photocathode 104 in the first dynode pathways 112a-112c of the first dynode channel 101a may experience no cross talk between the adjacent pathways.

It is also noted herein that the number of the dynode stages 108a-108c associated with the first dynode pathways 112a-112c of the first dynode channel 101a and the second dynode pathways 113a-113b of the second dynode channel 101b is not limited to the number of the dynode stages 108a-108c illustrated in FIG. 1B. The number of the plurality of the dynode stages 108a-108c depicted in FIG. 1B is provided merely for purposes of illustration and it is contemplated that any number of the dynode stages 108a-108c may be utilized in the present disclosure.

Figure 1C:
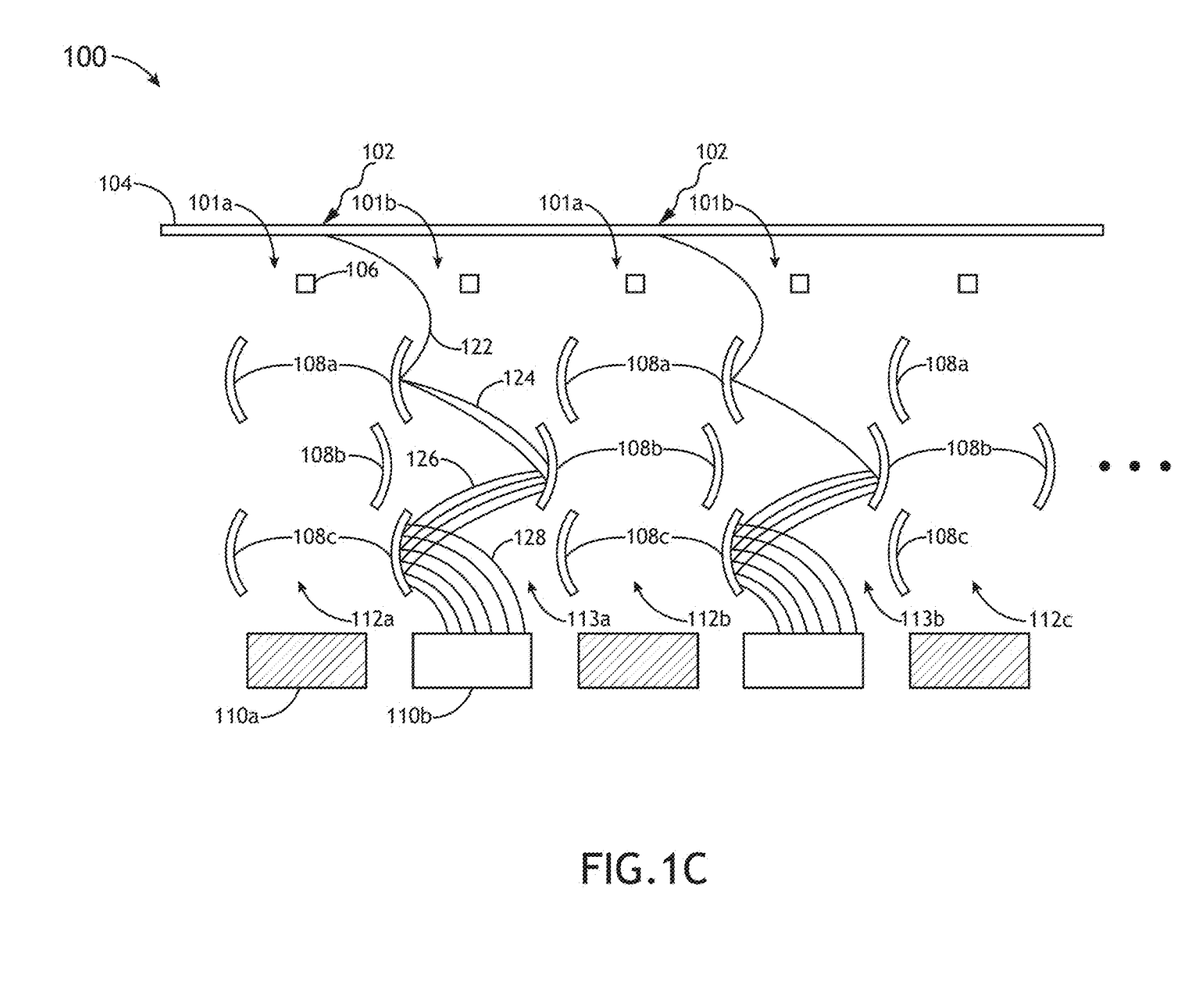
FIG. 1C illustrates a simplified schematic view of a multi-channel photomultiplier tube detector assembly depicting amplification of one or more portions of second photoelectrons in a second dynode channel, in accordance with one or more embodiments of the present disclosure.

FIG. 1C illustrates a simplified schematic view of the multi-channel PMT detector assembly 100 depicting amplification of the one or more portions of second photoelectrons 122 emitted by the photocathode 104 in the second dynode pathways 113a-113b of the second channel 101b, in accordance with one or more embodiments of the present disclosure. It is noted herein that the various embodiments, components and architecture described previously herein should be interpreted to extend to the multi-channel PMT detector assembly 100 of FIG. 1C.

It is noted that the one or more portions of the second photoelectrons 122 emitted by the photocathode 104 may reach the first set of the plurality of the dynode stages 108a associated with all of the second dynode pathways 113a-113b of the second dynode channel 101b at the same time, while the first dynode pathways 112a-112c of the first dynode channel 101a does not receive the first and/or second portions of the photoelectrons 122 by the photocathode 104. In this regard, the one or more portions of the second photoelectrons 122 emitted by the photocathode 104 in the second dynode pathways 113a-113b of the second dynode channel 101b may experience no cross talk between the adjacent pathways.

In another embodiment, the multi-channel PMT detector assembly 100 includes the plurality of the dynode stages 108a-108c associated with the first dynode pathways 112a-112c of the first dynode channel 101a and the second dynode pathways 113a-113b of the second dynode channel 101b. For example, the plurality of the dynode stages 108a-108c may be disposed along the first dynode pathways 112a-112c of the first dynode channel 101a and the second dynode pathways 113a-113b of the second dynode channel 101b. By way of another example, each of the first dynode pathways 112a-112c of the first dynode channel 101a and the second dynode pathways 113a-113b of the second dynode channel 101b may be divided by the plurality of the dynode stages 108a-108c. For instance, the plurality of the dynode stages 108a-108c may be stacked vertically along the dynode pathways in order to segregate each of the dynode pathways. In another instance, the plurality of the dynode stages 108a-108c may be disposed as a staggered arrangement along the dynode pathways. In this regard, each pathway (112a, 112b, 112c, 113a, or 113b) may be divided to effectively eliminate and/or reduce cross talks of the photoelectrons with neighboring photoelectron currents.

It is contemplated that, while the shape of the plurality of the dynode stages 108a-108c associated with the first dynode pathways 112a-112c of the first dynode channel 101a and the second dynode pathways 113a-113b of the second dynode channel 101b described above is shown as a dynode with a single curvature on the surface from the simplified view shown in FIGS. 1A-1C, such a configuration is merely provided for illustrative purposes. Other shapes of the plurality of the dynode stages 108a-108c such as a dynode with multiple curvatures on the surface may also be utilized. It is further contemplated that, while each set of the dynode stages 108a-108c described above is shown as separated metal pieces from the simplified view shown in FIGS. 1A-1C, such a configuration is merely provided for illustrative purposes. Other types of dynode stages such as a linear continuous dynode stage in the case of a continuous dynode type multiplier may also be utilized.

It is contemplated that, while the plurality of the dynode stages 108a-108c associated with all of the dynode pathways (112a, 112b, 112c, 113a, and 113b) described above are shown as a three piece dynode construction from the simplified view shown in FIGS. 1A-1C, such a configuration is merely provided for illustrative purposes. Other constructions of the plurality of the dynode stages 108a-108c such as a stack of a four or more piece dynode construction may also be utilized. In general, a typical PMT detector amplifies photoelectrons current ranging from 10 to as much as $10^8$ times prior to entering anodes by multiplying the photoelectrons from the photocathode 104 with up to 19 dynode stages.

It is further contemplated that, while the plurality of the dynode stages 108a-108c described above are arranged in a staggered arrangement from the simplified view shown in FIGS. 1A-1C, such an arrangement is merely provided for illustrative purposes. Other arrangements of the plurality of the dynode stages 108a-108c such as an eclipsed pattern may also be utilized.

In another embodiment, the multi-channel PMT detector assembly 100 includes a grid 106 for controlling and/or directing the one or more portions of the first and second photoelectrons 114, 122 emitted by the photocathode 104 into each of the first dynode pathways 112a-112c of the first dynode channel 101a and the second dynode pathways 113a-113b of the second dynode channel 101b via a voltage switching process with the first set of the plurality of the dynode stages 108a in each of the first dynode pathways 112a-112c of the first dynode channel 101a and the second dynode pathways 113a-113b of the second dynode channel 101b, respectively.

For example, the voltage switching process on the grid 106 and the first set of the plurality of the dynode stages 108a associated with the first dynode pathways 112a-112c of the first dynode channel 101a may be turned on to control and/or direct the one or more portions of the first photoelectrons 114 emitted by the photocathode 104 into the first dynode pathways 112a-112c of the first dynode channel 101a. By way of another example, the voltage switching process on the grid 106 and the first set of the plurality of the dynode stages 108a associated with the second dynode pathways 113a-113b of the second dynode channel 101b may be turned on to control and/or direct the one or more portions of the second photoelectrons 122 emitted by the photocathode 104 to the second dynode pathways 113a-113b of the second dynode channel 101b. For instance, the grid 106 may control, direct, and/or steer the one or more portions of the first and second photoelectrons 114, 122 by alternating between the first dynode pathways 112a-112c of the first dynode channel 101a and the second dynode pathways 113a-113b of the second dynode channel 101b. It is noted that the action of controlling, directing and/or steering the one or more portions of the first and second photoelectrons 114, 122 emitted by the photocathode 104 into the first dynode pathways 112a-112c of the first dynode channel 101a and/or the second dynode pathways 113a-113b of the second dynode channel 101b via the voltage switching process may be employed rapidly and/or repeatedly. It is further noted that the interval of the voltage switching process for controlling, directing, and/or steering the one or more portions of the first and second photoelectrons 114, 122 may be regular or irregular in nature.

Figure 1D:
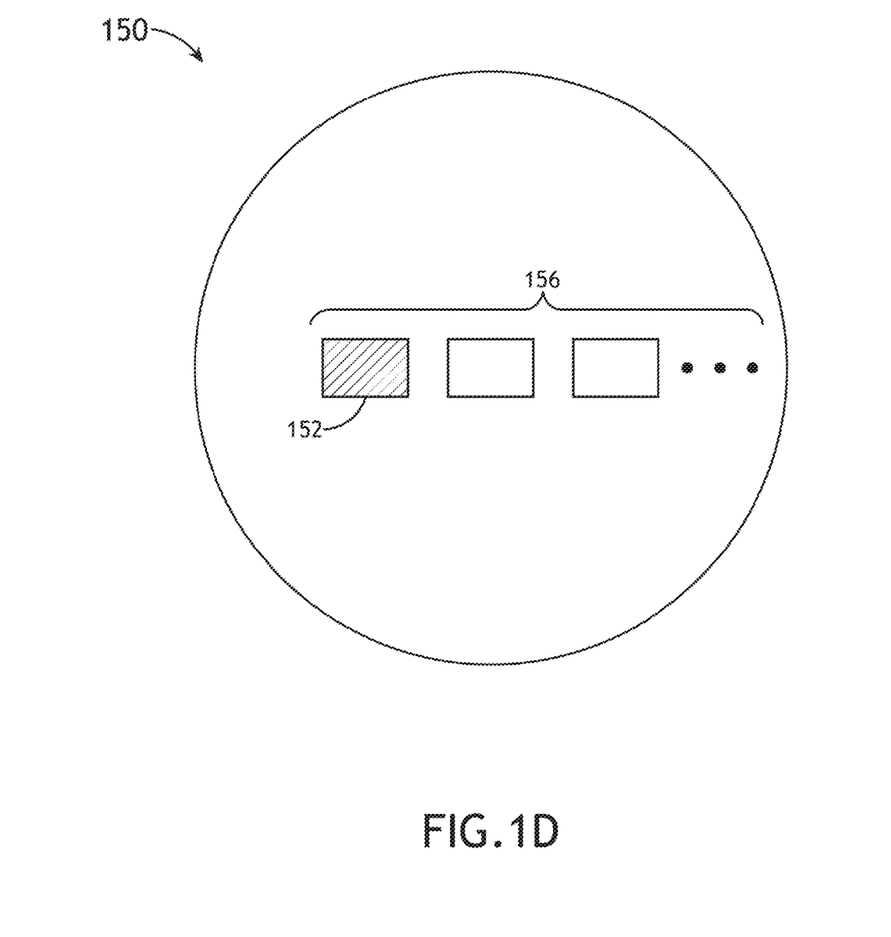
FIG. 1D illustrates a simplified schematic view of a sample inspection area with a first pixel, in accordance with one or more embodiments of the present disclosure.

FIG. 1D illustrates a simplified schematic view of an inspection area 150 of a sample, in accordance with one or more embodiments of the present disclosure. In one embodiment, the inspection area 150 includes illumination spots 156. For example, the illumination spots 156 may include a first pixel 152. By way of another example, the first pixel 152 may be a source for the photon 102 depicted in FIG. 1B responsible for the one or more portions of the first photoelectron 114. The multi-channel structure of the present disclosure allows user(s) to inspect adjacent samples or different areas of the same sample via multi-channel PMT detector assembly 100. In this regard, upon an illumination of the sample, the first pixel 152 in the inspection area 150 may be reflected, scattered, and/or diffracted from the sample as the photon 102 and then directed to the photocathode 104 of the multi-channel PMT detector assembly 100. The photocathode 104 may absorb the photon 102 and, in response to absorption of the photon 102, emit the one or more portions of the first photoelectrons 114. For instance, the one or more portions of the first photoelectrons 114 emitted by the photocathode 104 may be controlled and/or directed to the first dynode pathways 112a-112c of the first dynode channel 101a. It is noted that the photons entering the first dynode pathways 112a-112c of the first dynode channel 101a as the one or more portions of the first photoelectron 114 through the photocathode 104 derive from the same pixel (e.g., the first pixel 152) of the sample in the inspection area 150. The number of illumination spots 156 depicted in FIG. 1D is provided merely for illustrative purposes and it is contemplated that any number of illustration spots may be utilized in the present disclosure. Furthermore, the location of the first pixel 152 depicted in FIG. 1D is provided merely for purposes of illustration and it is contemplated that any location of the first pixel may be utilized in the present disclosure.

Figure 1E:
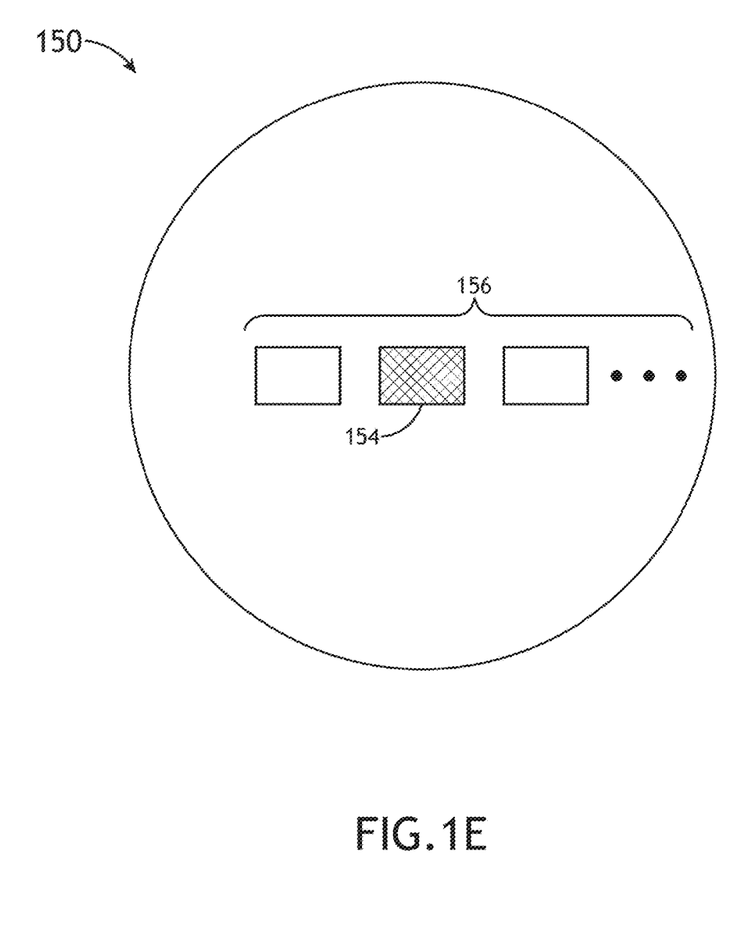
FIG. 1E illustrates a simplified schematic view of a sample inspection area with a second pixel, in accordance with one or more embodiments of the present disclosure.

FIG. 1E illustrates a simplified schematic view of an inspection area 150 of a sample, in accordance with one or more embodiments of the present disclosure. In one embodiment, the inspection area 150 includes illumination spots 156. For example, the illumination spots 156 may include a second pixel 154. By way of another example, the second pixel 154 may be a source for the photon 102 depicted in FIG. 1C responsible for the one or more portions of the second photoelectrons 122. The multi-channel structure of the present disclosure allows user(s) to inspect adjacent samples or different areas of the same sample via multi-channel PMT detector assembly 100. In this regard, upon an illumination of the sample, the second pixel 154 in the inspection area 150 may be reflected, scattered, and/or diffracted from the sample as the photon 102 and then directed to the photocathode 104 of the multi-channel PMT detector assembly 100. The photocathode 104 may absorb the photon 102 and, in response to absorption of the photon 102, emit the one or more portions of the second photoelectrons 122. For instance, the one or more portions of the second photoelectrons 122 emitted by the photocathode 104 may be controlled and/or directed to the second dynode pathways 113a-113b of the second dynode channel 101b. It is noted that the photons entering the second dynode pathways 113a-113b of the second dynode channel 101b as the one or more portions of the second photoelectron 122 through the photocathode 104 derive from the same pixel (e.g., the second pixel 154) of the sample in the inspection area 150. The number of illumination spots 156 depicted in FIG. 1E is provided merely for purposes of illustration and it is contemplated that any number of illustration spots may be utilized in the present disclosure. Furthermore, the location of the second pixel 154 depicted in FIG. 1E is provided merely for purposes of illustration and it is contemplated that any location of the first pixel may be utilized in the present disclosure.

Figure 1F:
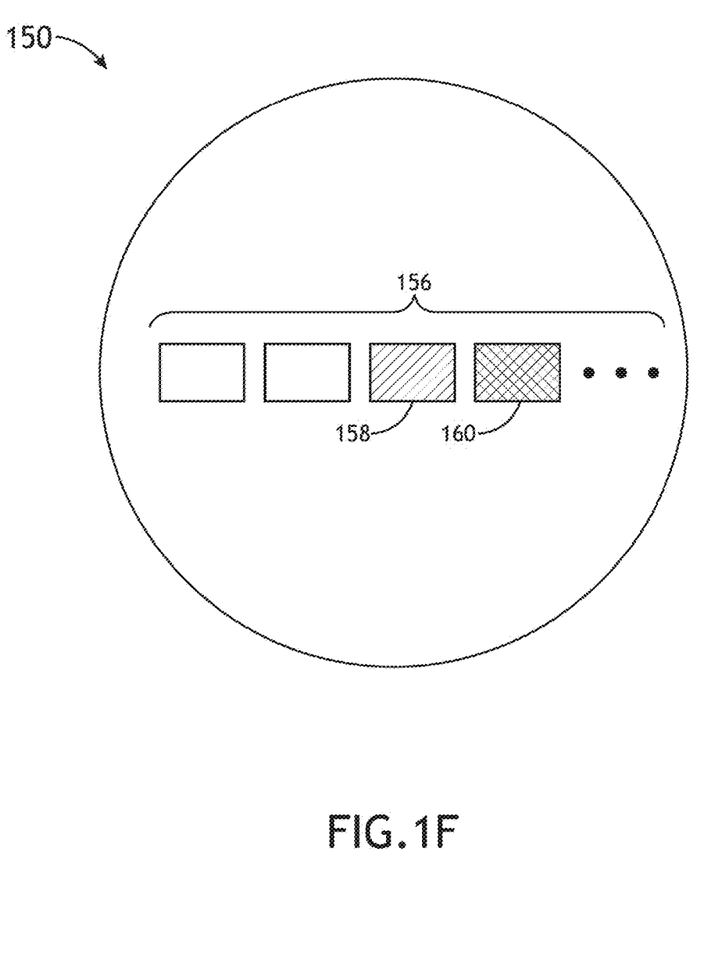
FIG. 1F illustrates a simplified schematic view of a sample inspection area with third and fourth pixels, in accordance with one or more embodiments of the present disclosure.

FIG. 1F illustrates a simplified schematic view of an inspection area 150 of a sample, in accordance with one or more embodiments of the present disclosure. In one embodiment, the inspection area 150 includes illumination spots 156. For example, the illumination spots 156 may include a third pixel 158 and a fourth pixel 160. It is noted that for the present disclosure every second pixel on the sample may be read by the anodes 110a-110b at a time. In this regard, an inspection of a new pair of pixels, the third pixel 158 and the fourth pixel 160, in the inspection area 150 may begin after a previous detection, the first pixel 152 and the second pixel 154, is completed. For instance, the photons from the third pixel 158 and the fourth pixel 160 may be absorbed by the photocathode 104 which, in response to the absorption of the photons, emits the corresponding one or more portions of the first and second photoelectrons (e.g., 114 and 122 shown in FIG. 1B and FIG. 1C, respectively). In another instance, the one or more portions of the first and second photoelectrons 114, 122 emitted by the photocathode 104 may be controlled and/or directed to the first dynode pathways 112a-112c of the first dynode channel 101a and the second dynode pathways 113a-113b of the second dynode channel 101b, respectively. In yet another instance, the one or more portions of the first and second photoelectrons 114, 122 generated from the third pixel 158 and the fourth pixel 160 through the photocathode 104 may be amplified in the first dynode pathways 112a-112c of the first dynode channel 101a and the second dynode pathways 113a-113b of the second dynode channel 101b via the plurality of the dynode stages 108a-108c, respectively.

Further, the corresponding amplified photoelectron current outputs 120, 128 may reach the first set of anode 110a and the second set of anode 110b to be detected. The process continues until it satisfies the inspection requirements. The number of illumination spots 156 depicted in FIG. 1F is provided merely for purposes of illustration and it is contemplated that any number of illustration spots may be utilized in the present disclosure. Furthermore, the locations of the third pixel 158 and the fourth pixel 160 depicted in FIG. 1F are provided merely for purposes of illustration and it is contemplated that any location of the third pixel 158 and the fourth pixel 160 may be utilized in the present disclosure.

Figure 2:
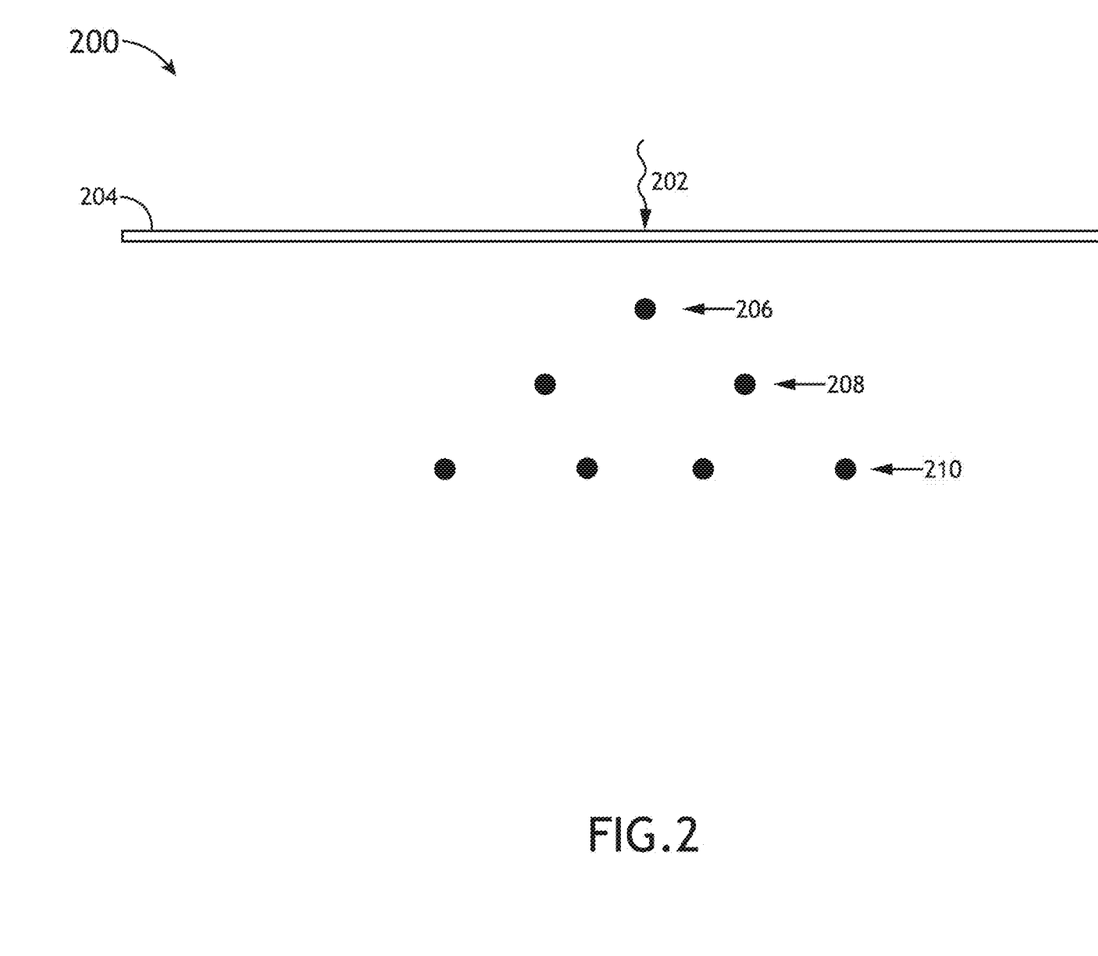
FIG. 2 illustrates a simplified schematic view of an alternative embodiment of the present disclosure, in accordance with one or more embodiments of the present disclosure.

FIG. 2 illustrates a simplified schematic view of a multi-channel PMT detector assembly 200, in accordance with one or more embodiments of the present disclosure. In another embodiment, the multi-channel PMT detector assembly 200 includes a photocathode 204 configured to absorb one or more photons 202. The features of the photocathode are previously described herein in the present disclosure. Further, the multi-channel PMT detector assembly 200 includes a series of grids (e.g., 206, 208, and 210). For example, the series of grids may include a first grid 206. When a photoelectron hits the first grid 206, the photoelectron may be steered onto a path via a voltage switching process. For instance, the series of grids may include a pair of second grids 208. Each of the grids 208 may function the same as the first grid 206. In this regard, the first photoelectron from the first grid 206 may encounter the grids 208. The grids 208 may then change path of the photoelectrons via the voltage switching process or allow them to continue their paths to another set of the grids depending on the inspection requirements.

Furthermore, in another embodiment, the series of grid includes a set of third grids 210 having four grids. For example, upon encountering the grids 210, the path of the photoelectron path(s) may be controlled depending on the voltage switching process. The photoelectrons may enter one or more dynode channels (not shown) followed by amplification via dynode stages (not shown) to provide amplified photoelectron outputs to be collected by one or more anodes (not shown). This process may continue until it satisfies the inspection requirements. It is noted that a multi-channel PMT detector assembly 200 may allow for precise control of photoelectron direction.

It is noted that the grids (206, 208, and 210) are positioned to follow a decision tree type structure where the number of grid increases as the number of rows increases according to the following relationship: $2^N$, where N represents the quantity (number of rows—1). For example, a first row may include one grid 206 ($2^{(0)}$). By way of another example, a second row may include two grids 208 ($2^{(1)}$). A third row and so on may have four grids 210 ($2^{(2)}$) and more. This continues until it satisfies the inspection requirements, cost, and some other factors. It is further noted that the number of anodes required for the alternative embodiment of the present disclosure depicted in FIG. 2 increases as the number of rows increases according to the following relationship: $2^M$, where M represents the quantity (number of rows). For example, a first row may include two anodes (e.g., first grid 206). By way of another example, a second row may include four anodes (e.g., the first grid 206 and the second grid 208). By way of yet another example, a third row may include eight anodes (e.g., the first grid 206, the second grid 208, and the third grid 210). This may continue until it satisfies the inspection requirements, cost, and some other factors. It is contemplated that, while the alternative embodiment of the present disclosure depicted in FIG. 2 shows three rows of grids (206, 208, and 210), other configurations such as four- or more-rows of grids may be utilized.

It is contemplated that, while the present disclosure focuses on a two-dimensional arrangement having two channels 101a, 101b in a parallel, the same principle may be extended to a three-dimensional arrangement having one set of two dynode channels 101a, 101b in one dimension and another set of two dynode channels 101a, 101b in another dimension. This would yield a total of four dynode channels PMT detector assembly in three-dimension. This would increase the speed of the multi-channel PMT detector 100 depicted in FIGS. 1A-1C by two times. It is noted that the numbers of dynode channels in one dimension and another dimension may be different. For example, the PMT detector may have two dynode channels in one dimension and three dynode channels in another dimension. It is further noted that the combinations of the numbers of the dynode channels in one and another dimensions may depend based on the inspection requirements.

Figure 3:
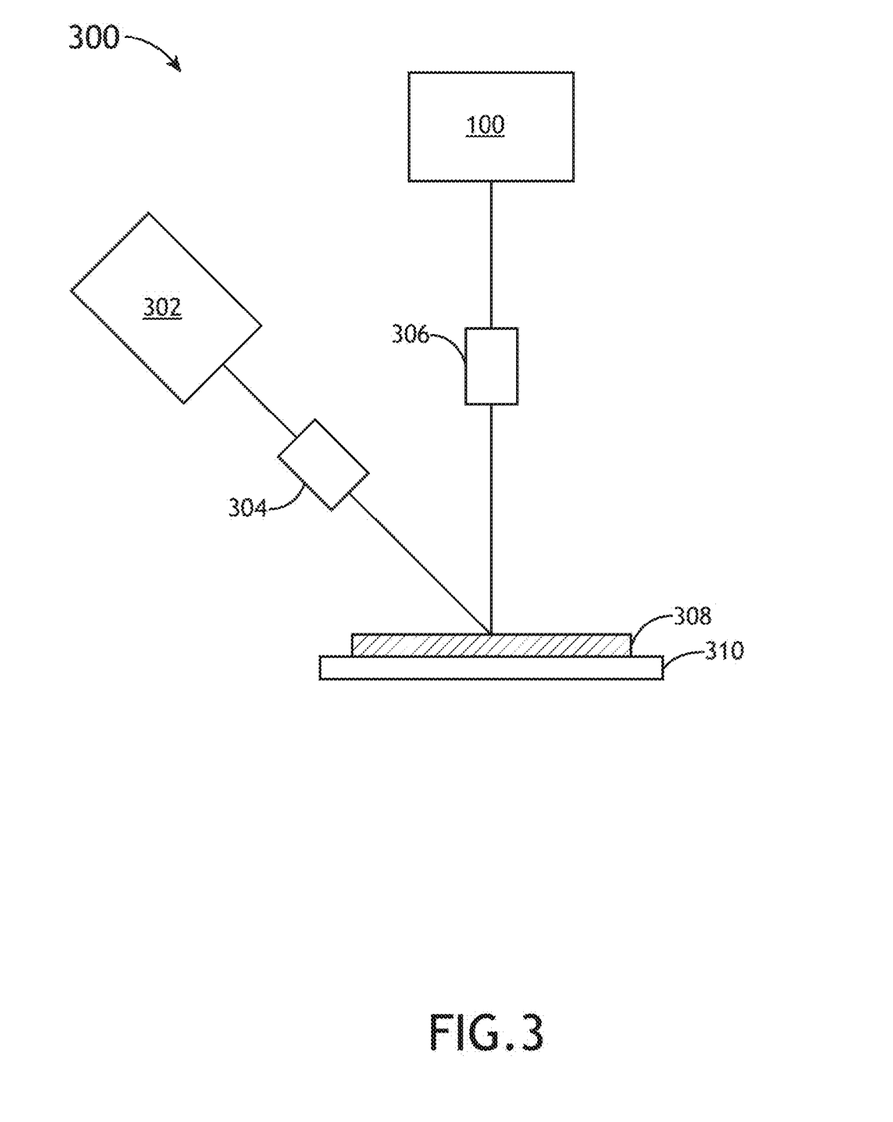
FIG. 3 illustrates a block diagram of an inspection system equipped with a multi-channel photomultiplier tube detector assembly, in accordance with one or more embodiments of the present disclosure.

FIG. 3 illustrates an inspection system 300 equipped with the multi-channel PMT detector assembly 100, in accordance with one or more embodiments of the present disclosure. In one embodiment, the inspection system 300 includes a multi-channel PMT based detector. In another embodiment, the multi-channel PMT based detector of the inspection system 300 includes a multi-channel PMT detector assembly 100. In this regard, the multi-channel PMT detector assembly 100 of the inspection system 300 includes a photomultiplier tube detector (as described previously herein); a photocathode configured to absorb photons, the photocathode further configured to emit photoelectrons; a first dynode channel, the first dynode channel including a first set of dynode pathways, at least some of the first set of dynode pathways including a plurality of dynode stages configured to receive a first portion of the photoelectrons and direct a first amplified photoelectron current onto a first anode of a first set of anodes; an additional dynode channel, the additional dynode channel including an additional set of dynode pathways, at least some of the additional set of dynode pathways including a plurality of dynode stages configured to receive an additional portion of the photoelectrons and direct an additional amplified photoelectron current onto an additional anode of an additional set of anodes; and a grid configured to direct the first portion of the photoelectrons emanating from the photocathode to one or more of the first set of pathways of the first dynode channel, wherein the grid is further configured to direct the additional portion of the photoelectrons emanating from the photocathode to one or more of the additional set of pathways of the additional dynode channel. In another embodiment, the multi-channel PMT detector assembly 100 of the inspection system 300 is configured to detect photons from a sample surface 308 through the set of collection optics 306.

In another embodiment, the inspection system 300 includes an illumination source 302 configured to illuminate a portion of a surface of a sample 308 (e.g., semiconductor wafer) disposed on a sample stage 310. For example, the inspection system 300 may be configured to operate in conjunction with any illumination source known in the art. For example, the illumination source used to illuminate the surface of the sample may include, but is not limited to, a broad band light source (e.g., xenon lamp, laser-sustained plasma lamp and the like). For example, the illumination source used to illumination the surface of the sample may include, but is not limited to, a narrow band light source (e.g., one or more lasers).

In another embodiment, the inspection system 300 includes a set of illumination optics 304 configured to direct and focus the illumination onto the sample surface. The illumination optics 304 of the inspection system 300 may include any illumination optics known in the art suitable for directing, processing, and/or focusing the light beam emanating from the illumination source 302 onto a portion of the surface of the sample 308. For example, the set of illumination optics 304 may include, but is not limited to, one or more lenses, one or more mirrors, one or more beam splitters, one or more polarizer elements, and the like.

In another embodiment, the inspection system 300 includes a set of collection optics 306 configured to direct and focus at least a portion of the light scattered from the surface of the sample 308 onto the multi-channel PMT photocathode 104 of the multi-channel PMT detector assembly 100. The collection optics 306 of the inspection system 300 may include any collection optics known in the art suitable for directing, processing, and/or focusing light scattered from the surface of the sample 308 onto the multi-channel PMT detector assembly 100. For example, the set of collection optics 306 may include, but are not limited to, one or more lenses, one or more mirrors, one or more beam splitters, one or more polarizer elements, and the like.

In another embodiment, it is contemplated herein that the illumination source 302, the illumination optics 304, the collection optics 306, and the multi-channel PMT detector assembly 100 are arranged in a dark field configuration such that the inspection system 300 operates as a dark field inspection system. In another embodiment, the inspection system 300 is configured to operate as a bright field inspection system (not shown).

It is contemplated that, while the illustrations shown in the present disclosure are based on a metal channel type dynode configuration for PMT detectors, the present disclosure can be utilized with most of the different dynode configurations currently used for PMT detectors.

It is noted that the main purpose of the present disclosure is to increase inspection bandwidth by avoiding and/or reducing cross talks between dynode channels in the multi-channel PMT detector assembly 100 so as to increase the inspection speed. It is commonly understood by a person with ordinary skill in the art that doubling the speed of electronics increases noise level by $\sqrt{2}$. It is further noted that the present disclosure may also give user(s) an option to keep the detector assembly speed constant while reducing the speed of electronics by factor of 2, which results in the reduction of noise level by $\sqrt{2}$. The present disclosure may enable user(s) to fine-tune the multi-channel PMT detector assembly 100 so as to accommodate various inspection requirements.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. Furthermore, it is to be understood that the invention is defined by the appended claims.

What is claimed is:

1. A photomultiplier tube detector assembly, comprising:
   a photocathode configured to emit photoelectrons in response to absorption of photons from a sample;
   a first dynode channel, the first dynode channel including a first set of dynode pathways, at least some of the first set of dynode pathways including a plurality of dynode stages configured to receive photoelectrons from the photocathode and direct a first amplified photoelectron current onto a first set of anodes to generate a first channel signal;
   an additional dynode channel, the additional dynode channel including an additional set of dynode pathways, at least some of the additional set of dynode pathways including a plurality of dynode stages configured to receive photoelectrons from the photocathode and direct an additional amplified photoelectron current onto an additional set of anodes to generate an additional channel signal, wherein the first dynode pathways and the additional dynode pathways are arranged in an interleaving parallel pattern; and
   a grid configured to selectively direct photoelectrons emanating from the photocathode to one of the first dynode channel or the additional dynode channel to selectively generate a first channel signal or an additional channel signal, wherein the grid is further configured to steer the photoelectrons from the photocathode into the first dynode channel or the additional dynode channel via a voltage switching process.

2. The photomultiplier tube detector assembly of claim 1, wherein the first set of anodes and the additional set of anodes are arranged in an interleaved pattern.

3. The photomultiplier tube detector assembly of claim 1, wherein the first set of anodes are positioned within the first set of dynode pathways of the first dynode channel.

4. The photomultiplier tube detector assembly of claim 1, wherein the additional set of anodes are positioned within the additional set of dynode pathways in the additional dynode channel.

5. The photomultiplier tube detector assembly of claim 1, wherein the grid is configured to alternately direct photoelectrons into the first dynode channel and the additional dynode channel.

6. The photomultiplier tube detector assembly of claim 1, wherein at least one of the first set of anodes or the additional set of anodes comprises:
   a first set of phosphor anodes configured to convert the photoelectrons to a first light signal or an additional set of phosphor anodes configured to convert the photoelectrons to an additional light signal.

7. The photomultiplier tube detector assembly of claim 6, further comprising:
   at least one of a first detector configured to detect the first light signal generated by the first set of phosphor anodes or an additional detector configured to detect the additional light signal generated by the additional set of phosphor anodes.

8. The photomultiplier tube detector assembly of claim 7, wherein at least one of the first detector or the additional detector comprises:
   at least one of a charge-coupled device (CCD) detector or a complementary metal oxide-semiconductor (CMOS) detector.

9. An inspection system, comprising:
   an illumination source configured to illuminate a portion of a sample surface;
   a set of illumination optics configured to direct and focus the illumination onto the sample surface; and
   a photomultiplier tube detector assembly, comprising:
      a photocathode configured to emit photoelectrons in response to absorption of the illumination;
      a first dynode channel, the first dynode channel including a first set of dynode pathways, at least some of the first set of dynode pathways including a plurality of dynode stages configured to receive photoelectrons from the photocathode and direct a first amplified photoelectron current onto a first set of anodes to generate a first channel signal, wherein the first portion of the photoelectrons is associated with a first portion of the sample;
      an additional dynode channel, the additional dynode channel including an additional set of dynode pathways, at least some of the additional set of dynode pathways including a plurality of dynode stages configured to receive photoelectrons from the photocathode and direct an additional amplified photoelectron current onto an additional set of anodes to generate an additional channel signal, wherein the first dynode pathways and the additional dynode pathways are arranged in an interleaving parallel pattern; and a grid configured to selectively direct photoelectrons emanating from the photocathode to one of the first dynode channel or the additional dynode channel to selectively generate a first channel signal or an additional channel signal, wherein the grid is further configured to steer the photoelectrons from the photocathode into the first dynode channel or the additional dynode channel via a voltage switching process.

10. The inspection system of claim 9, wherein the first set of anodes and the additional set of anodes are arranged in an interleaved pattern.

11. The inspection system of claim 9, wherein the first set of anodes are positioned within the first set of dynode pathways of the first dynode channel.

12. The inspection system of claim 9, wherein the additional set of anodes are positioned within the additional set of dynode pathways in the additional dynode channel.

13. The inspection system of claim 9, wherein the grid is configured to alternately direct photoelectrons into the first dynode channel and the additional dynode channel.

14. The inspection system of claim 9, wherein the illumination source is a broad band light source.

15. The inspection system of claim 9, wherein the illumination source is a narrow band light source.

16. The inspection system of claim 9, wherein at least one of the first set of anodes or the additional set of anodes comprises: a first set of phosphor anodes configured to convert the photoelectrons to a first light signal or an additional set of phosphor anodes configured to convert the photoelectrons.

17. The inspection system of claim 16, further comprising:

at least one of a first detector configured to detect the first light signal generated by the first set of phosphor anodes or an additional detector configured to detect the additional light signal generated by the additional set of phosphor anodes.

18. The inspection system of claim 17, wherein at least one of the first detector or the additional detector comprises:

at least one of a charge-coupled device (CCD) detector or a complementary metal oxide-semiconductor (CMOS) detector.

* * * * *